(12) United States Patent
Yang

(10) Patent No.: US 12,110,149 B2
(45) Date of Patent: Oct. 8, 2024

(54) LIFTABLE AND FOLDABLE DISINFECTION BOX

(71) Applicant: XIAMEN BABY PRETTY PRODUCTS CO., LTD., Xiamen (CN)

(72) Inventor: Jianbo Yang, Xiamen (CN)

(73) Assignee: XIAMEN BABY PRETTY PRODUCTS CO., LTD., Xiamen (CN)

( * ) Notice: Subject to any disclaimer, the term of this patent is extended or adjusted under 35 U.S.C. 154(b) by 580 days.

(21) Appl. No.: 17/389,376

(22) Filed: Jul. 30, 2021

(65) Prior Publication Data

US 2022/0194658 A1   Jun. 23, 2022

(30) Foreign Application Priority Data

Dec. 21, 2020   (CN) .......................... 202023102361.7

(51) Int. Cl.
*B65D 21/08* (2006.01)
*A61L 2/10* (2006.01)

(52) U.S. Cl.
CPC .............. *B65D 21/086* (2013.01); *A61L 2/10* (2013.01); *A61L 2202/11* (2013.01); *A61L 2202/122* (2013.01); *A61L 2202/14* (2013.01)

(58) Field of Classification Search
CPC .. B65D 21/086; B65D 11/18; A61L 2202/122
See application file for complete search history.

(56) References Cited

U.S. PATENT DOCUMENTS

| | | | | |
|---|---|---|---|---|
| 968,633 | A | * | 8/1910 | Andrews .............. B65D 21/086 232/14 |
| 3,338,388 | A | * | 8/1967 | Igoe ..................... B65D 21/086 223/66 |
| 6,010,022 | A | * | 1/2000 | Deaton ............. B65D 77/0466 220/666 |
| D952,894 | S | * | 5/2022 | Zhang ......................... D24/217 |
| D972,165 | S | * | 12/2022 | Yang ............................ D24/217 |
| 2007/0241104 | A1 | * | 10/2007 | Huizingh ............. B65D 21/086 220/8 |
| 2017/0332821 | A1 | * | 11/2017 | Maurello .............. A47J 27/002 |
| 2018/0177344 | A1 | * | 6/2018 | Bagley ................. B65D 21/086 |
| 2019/0359382 | A1 | * | 11/2019 | Frankenberg ....... B65D 21/0219 |
| 2021/0046198 | A1 | * | 2/2021 | Winslow .................. A61L 2/26 |
| 2021/0147114 | A1 | * | 5/2021 | Nyul ..................... B65D 85/20 |
| 2021/0171237 | A1 | * | 6/2021 | Hsu ...................... B65D 21/086 |
| 2021/0275708 | A1 | * | 9/2021 | Weiss ................... A61C 8/0087 |

(Continued)

*Primary Examiner* — Don M Anderson
(74) *Attorney, Agent, or Firm* — Bayramoglu Law Offices LLC

(57) ABSTRACT

A liftable and foldable disinfection box includes an upper half box body and a lower half box body. The upper half box body is sleeved on the lower half box body in a relatively liftable manner. A positioning mechanism is mounted in a lifting stroke of the upper half box body. The upper half box body and the lower half box body are fixed by locking the positioning mechanism, or the upper half box body is liftable relative to the lower half box body by unlocking the positioning mechanism. A disinfection chamber for receiving objects is formed between the upper half box body and the lower half box body. The disinfection chamber has a chamber door. The disinfection box can be folded in a liftable manner to facilitate carrying and prompt or timely disinfection.

7 Claims, 5 Drawing Sheets

(56) References Cited

U.S. PATENT DOCUMENTS

| | | | |
|---|---|---|---|
| 2022/0194658 A1* | 6/2022 | Yang | A61L 2/10 |
| 2022/0218859 A1* | 7/2022 | Chen | A61L 2/26 |
| 2022/0315283 A1* | 10/2022 | Kersley | B65D 55/02 |
| 2022/0379939 A1* | 12/2022 | Codispoti | B65D 21/086 |
| 2023/0200558 A1* | 6/2023 | Yang | A47D 9/012 5/98.1 |

* cited by examiner

LIFTABLE AND FOLDABLE DISINFECTION BOX

CROSS REFERENCE TO THE RELATED APPLICATIONS

This application is based upon and claims priority to Chinese Patent Application No. 202023102361.7, filed on Dec. 21, 2020, the entire contents of which are incorporated herein by reference.

TECHNICAL FIELD

The present invention relates to a disinfection box that can be folded in a liftable manner.

BACKGROUND

Generally, devices used for the disinfection of objects, such as disinfection cabinets and disinfection boxes, are relatively large in size. In this case, these disinfection devices are typically fixedly placed at a certain position in a room, and thus are not convenient to move around or even carry around. Since the prevalence of Corona Virus Disease 2019 (COVID-19) in early 2020, more and more people raise their awareness of hygiene, paying more attention to the timely disinfection of daily necessities, such as mobile phones, glasses, masks and keys, so as to reduce the spread of germs. However, existing disinfection devices cannot meet the needs of being portable and prompt or timely disinfection. In view of this, it is highly desirable to develop a foldable disinfection box to facilitate carrying and the convenience of prompt or timely disinfection.

SUMMARY

In order to solve the above-mentioned problems, the present invention provides a liftable and foldable disinfection box that can be folded in a liftable manner to facilitate carrying and timely disinfection.

In order to achieve the above-mentioned objective, the present invention provides the following technical solution.

A liftable and foldable disinfection box includes an upper half box body and a lower half box body. The upper half box body is sleeved on the lower half box body in a relatively liftable manner. A positioning mechanism is mounted in a lifting stroke of the upper half box body. The upper half box body and the lower half box body are fixed by locking the positioning mechanism, or the upper half box body is liftable relative to the lower half box body by unlocking the positioning mechanism. A disinfection chamber for receiving objects is formed between the upper half box body and the lower half box body. The disinfection chamber has a chamber door.

Further, the relatively liftable manner includes: sleeving the peripheral side wall of the upper half box body outside the peripheral side wall of the lower half box body; and forming a rib and a groove fitting with each other on the peripheral side wall of the upper half box body and the peripheral side wall of the lower half box body, wherein the rib and the groove extend along a vertical direction, and the rib is slidably fitted in the groove to enable the upper half box body to be liftable relative to the lower half box body.

Further, a plurality of sets of ribs and grooves are formed on the upper half box body and the lower half box body. The plurality of sets of ribs and grooves are evenly distributed on the peripheral side wall of the upper half box body and the peripheral side wall of the lower half box body. The positioning mechanism is mounted on at least one set of the plurality of sets of ribs and grooves.

Further, the positioning mechanism includes a rack track, a toothed block and a pressing block. The rib is formed on the upper half box body, and the rib has a hollow tube. The bottom of the hollow tube is closed and the top of the hollow tube has an opening. The opening is located on the top surface of the upper half box body. The side surface at the bottom of the hollow tube has a side opening. The lower half box body has a groove. The rack track is formed on the inner wall of the groove corresponding to the side opening at the bottom of the hollow tube. The toothed block is disposed at the bottom of the hollow tube. An elastic member such as a spring is disposed between the toothed block and the inner wall of the hollow tube. Under the action of the elastic member, an engaging tooth of the toothed block extends from the side opening at the bottom of the hollow tube and fits with the rack track. A lower inclined pushing surface is formed on the upper portion of the toothed block. The pressing block is inserted into the hollow tube. The upper end of the pressing block is located at the opening of the hollow tube to facilitate a pressing operation. An upper inclined pushing surface is formed at the lower end of the pressing block. The upper inclined pushing surface fits with the lower inclined pushing surface, so that when the pressing block is pressed, the toothed block is driven to overcome the action of the elastic member, so that the engaging tooth is separated from the rack track.

Further, a guide block is formed in the middle of the upper portion of the toothed block, and the lower inclined pushing surface is formed on each of both sides of the guide block. A guide groove is formed in the middle of the lower end of the pressing block, and the upper inclined pushing surface is formed on each of both sides of the guide groove. When the upper inclined pushing surface fits with the lower inclined pushing surface, the guide block is located in the guide groove.

Further, a mounting opening, a cover plate and a mounting block are formed at a lower section of the hollow tube. The cover plate is disposed at the mounting opening. The side opening from which the engaging tooth of the toothed block extends out is located under the cover plate. The cover plate is fixed on the mounting block by a fastener such as a screw. The mounting block is located above the toothed block and in the guide groove of the pressing block.

Further, a limiting step is formed at the inner wall of the hollow tube. A limiting convex ring is formed at the outer surface of the pressing block. The limiting step fits with the limiting convex ring, so that the pressing block is limited in the hollow tube.

Further, an anti-release mechanism is mounted on at least one of the plurality of sets of ribs and grooves. The upper portion of the groove is provided with an upper baffle, and the lower portion of the rib is provided with a lower baffle. The upper baffle and the lower baffle constitute the anti-release mechanism. The upper baffle abuts against the lower baffle, so that the rib is limited in the groove.

Further, an upper arc edge is formed on the upper half box body, and a lower arc edge is formed on the lower half box body. When the upper half box body and the lower half box body are folded, the upper arc edge is attached to the lower arc edge, and a forcing groove into which a hand extends is formed at each of a position of the upper arc edge and a position of the lower arc edge corresponding to the pressing block.

Further, a battery, a switch, a circuit board and an ultraviolet generator are mounted at the bottom of the lower half box body. The battery supplies power to the circuit board and the ultraviolet generator through the switch, and the circuit board controls the ultraviolet generator to work or stop.

By means of the above technical solution of the present invention, the upper half box body and the lower half box body are designed to be foldable in a liftable manner. When not in use, the upper half box body can be lowered relative to the lower half box body to be folded, and then the upper half box body and the lower half box body are positioned to a minimum volume by the positioning mechanism to facilitate packaging, storing and carrying. When in use, the upper half box body can be lifted relative to the lower half box body to be unfolded, and then the upper half box body and the lower half box body are positioned to a proper volume by the positioning mechanism to facilitate disinfection processing on the objects received in the disinfection chamber, which is convenient to use.

Figure 1:
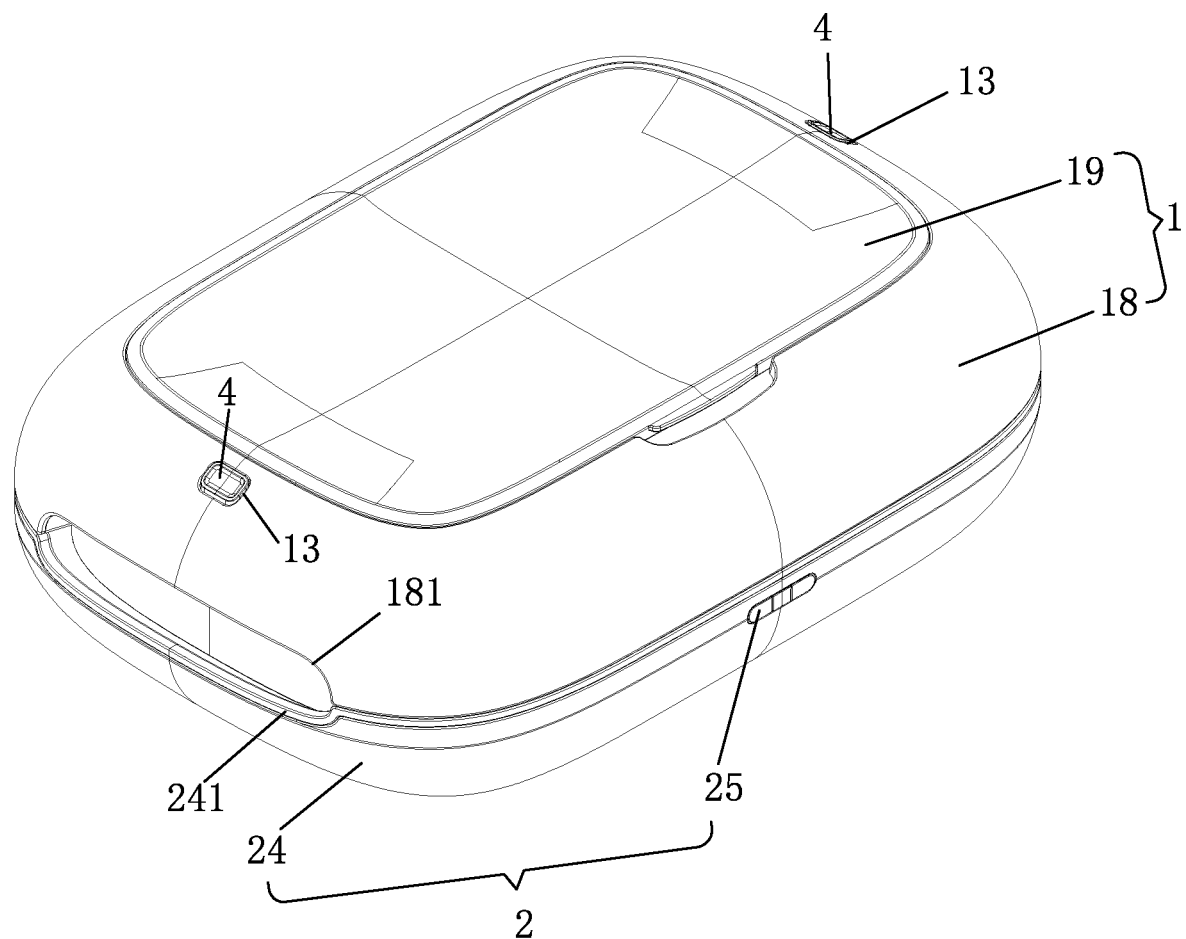
FIG. 1 is a schematic view of a folded state of the present invention.
Figure 2:
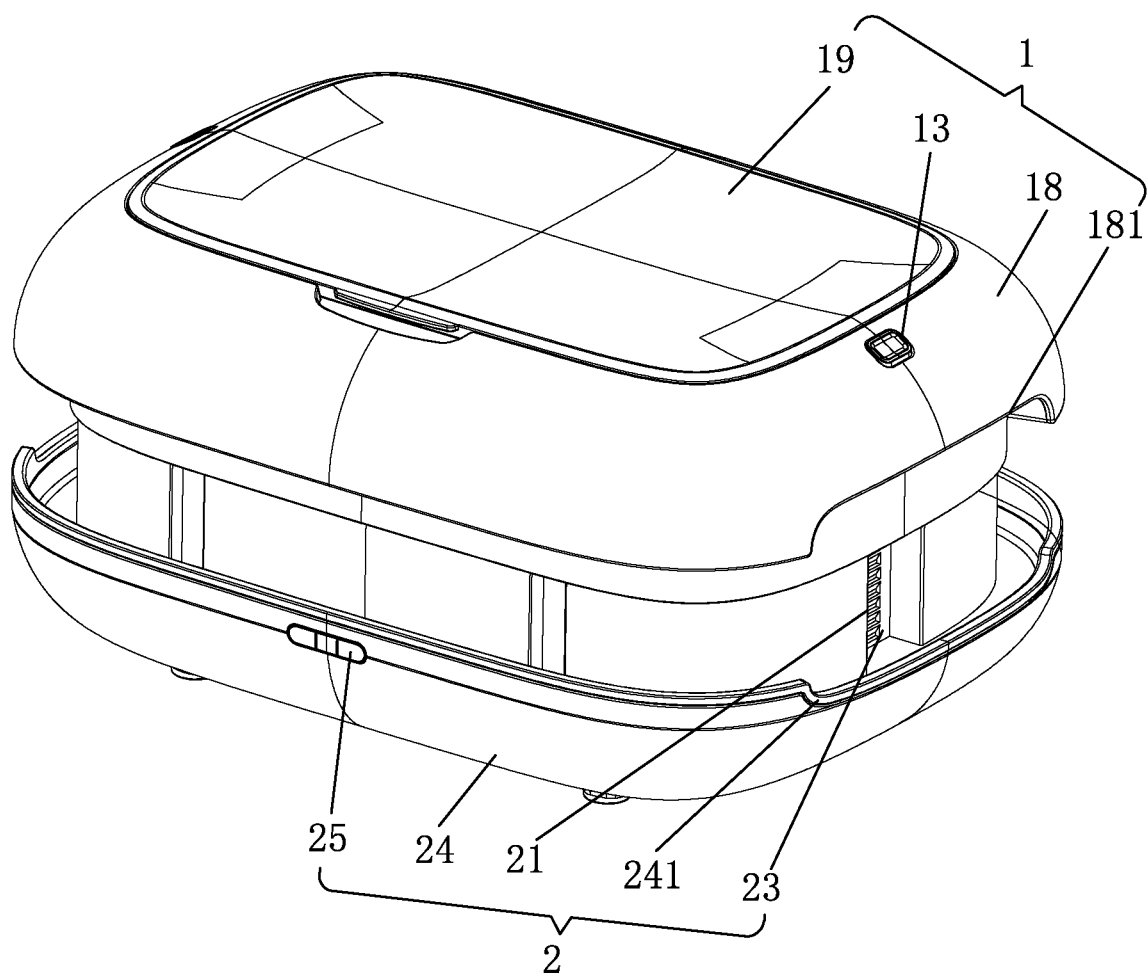
FIG. 2 is a schematic view of an unfolded state of the present invention.
Figure 3:
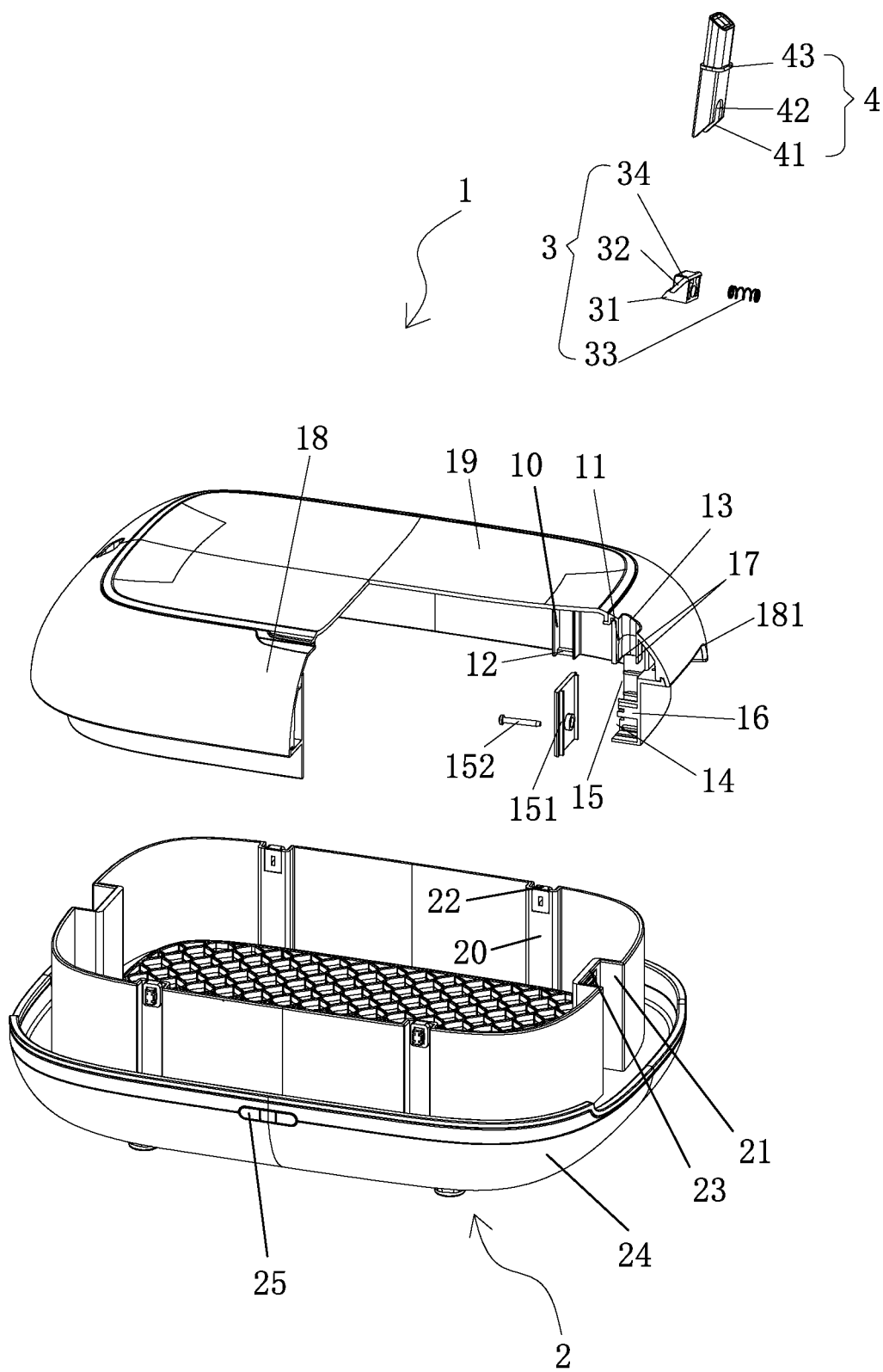
FIG. 3 is an exploded view of the present invention.
Figure 4:
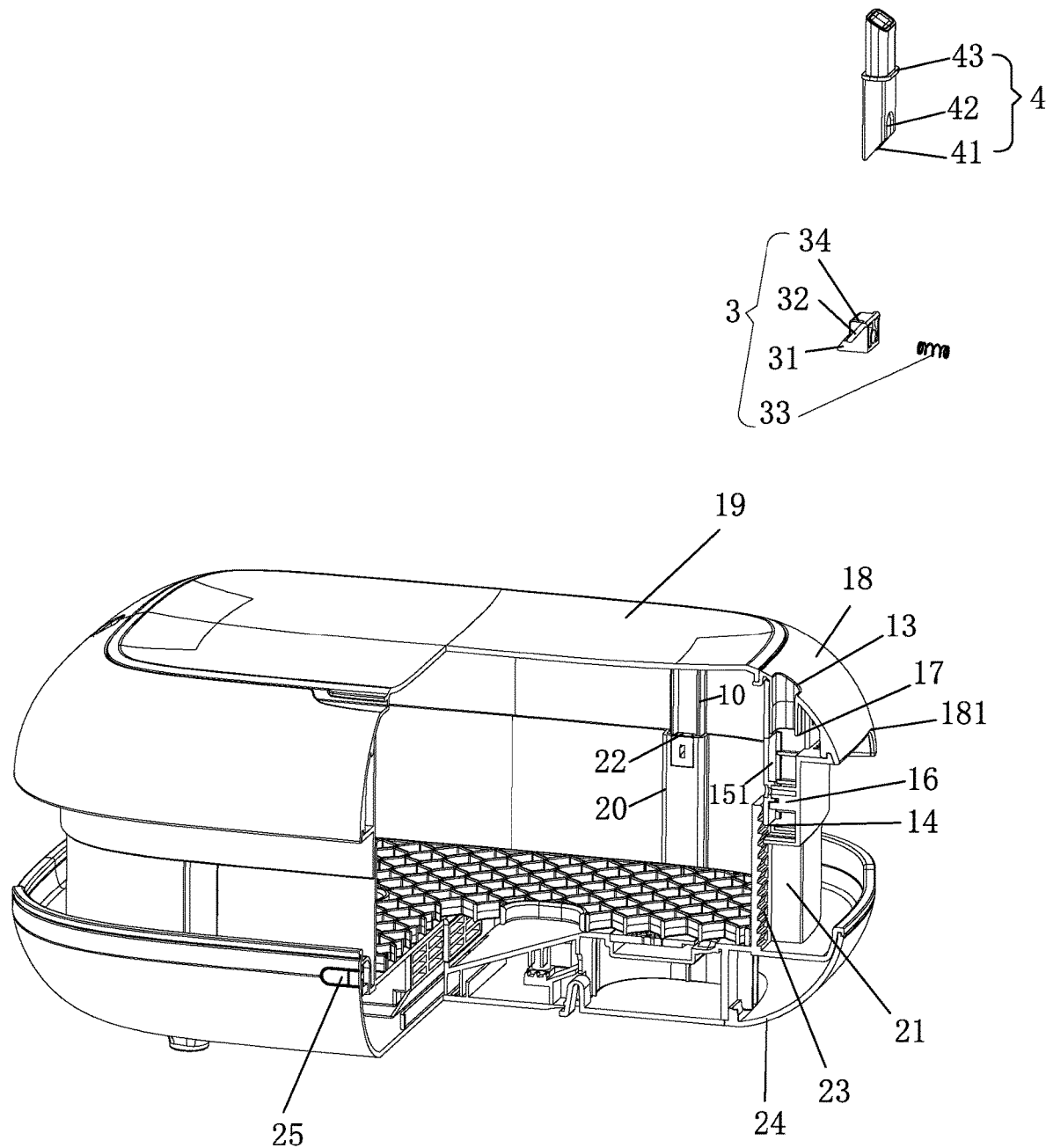
FIG. 4 is an exploded view of the present invention in an assembled state.
Figure 5:
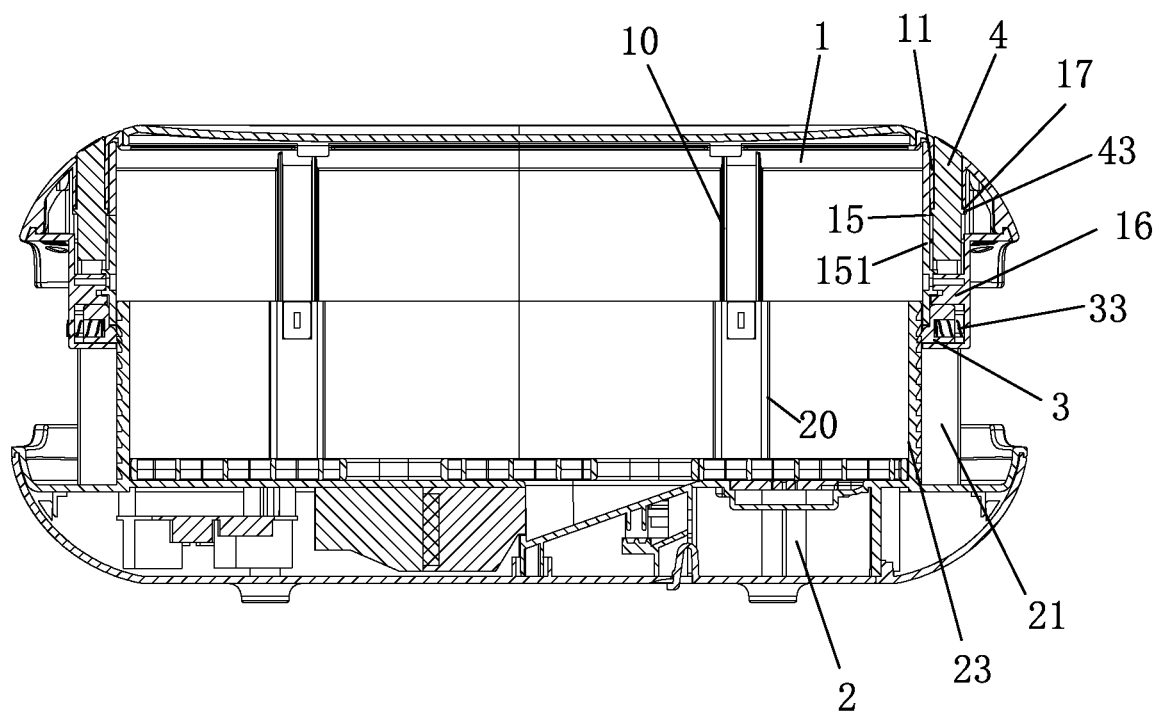
FIG. 5 is a cross-sectional view of the present invention in the assembled state.

IN THE FIGURES 1, upper half box body; 10 and 11, rib; 12, lower baffle; 13, opening; 14, side opening; 15, mounting opening; 151, cover plate; 152, fastener; 16, mounting block; 17, limiting step; 18, upper arc edge; 181, forcing groove; 19, chamber door;

2, lower half box body; 20 and 21, groove; 22, upper baffle; 23, rack track; 24, lower arc edge; 241, forcing groove; 25, switch;

3, toothed block; 31, engaging tooth; 32, lower inclined pushing surface; 33, elastic member; 34, guide block;

4, pressing block; 41, upper inclined pushing surface; 42, guide groove; and 43, limiting convex ring.

DETAILED DESCRIPTION OF THE EMBODIMENTS

For further explanation, the present invention provides the drawings. As part of the contents disclosed by the present invention, these drawings are mainly used to explain the embodiments, and can interpret the operation principles of the embodiments in conjunction with the related depictions of the description. With reference to these contents, those ordinary skilled in the art should understand other possible embodiments and advantages of the present invention. The components in the drawings are not drawn to scale, and similar component symbols are generally used to indicate similar components.

The present invention is further explained below in conjunction with the drawings and specific embodiments.

Referring to FIGS. 1-5, according to the present embodiment, a liftable and foldable disinfection box includes the upper half box body 1 and the lower half box body 2. The upper half box body 1 is sleeved on the lower half box body 2 in a relatively liftable manner. A positioning mechanism is mounted in a lifting stroke of the upper half box body 1. The upper half box body 1 and the lower half box body 2 are fixed by locking the positioning mechanism, or the upper half box body 1 is liftable relative to the lower half box body 2 by unlocking the positioning mechanism. A disinfection chamber is formed between the upper half box body 1 and the lower half box body 2. The disinfection chamber is configured to receive objects to perform disinfection processing, and the disinfection chamber has the chamber door 19. When the disinfection box is not in use, the upper half box body 1 can be lowered relative to the lower half box body 2 to be folded together with the lower half box body 2, and then the upper half box body 1 and the lower half box body 2 are positioned to a minimum volume by the positioning mechanism to facilitate packaging, storing and carrying. When the disinfection box is in use, the upper half box body 1 can be lifted relative to the lower half box body 2 to be unfolded, and then the upper half box body 1 and the lower half box body 2 are positioned to a proper volume (which is a maximum volume or a larger volume than the volume in the folded state, and can be specifically determined according to the size and number of objects that need to be disinfected) by the positioning mechanism. In this way, it is convenient to perform disinfection processing on the objects received in the disinfection chamber, which is user-friendly.

The relatively liftable manner in the present invention, as shown in the figures, is not limited to the structure shown in the figures, and specifically includes: sleeving the peripheral side wall of the upper half box body 1 outside the peripheral side wall of the lower half box body 2; forming the ribs 10 and 11 on the peripheral side wall of the upper half box body 1, and forming the grooves 20 and 21 on the peripheral side wall of the lower half box body 2, wherein the ribs 10 and 11 and the grooves 20 and 21 fit with each other and extend along the vertical direction, and the ribs 10 and 11 are slidably fitted in the grooves 20 and 21 to enable the upper half box body 1 to be liftable relative to the lower half box body 2.

In order to ensure a smooth folding operation, in the present invention, a plurality of sets of ribs 10, 11 and grooves 20, 21 are formed on the upper half box body 1 and the lower half box body 2. The plurality of sets of ribs 10, 11 and grooves 20, 21 are evenly distributed on the peripheral side wall of the upper half box body 1 and the peripheral side wall of the lower half box body 2. The positioning mechanism is mounted on at least one set of the rib 11 and the groove 21. In the present embodiment, two positioning mechanisms are mounted on two sets of ribs 11 and grooves 21 that are disposed symmetrically. Moreover, in the present invention, an anti-release mechanism is further disposed on at least one set of the rib 10 and the groove 20. The upper portion of the groove 20 is provided with the upper baffle 22, and the lower portion of the rib 10 is provided with the lower baffle 12. The upper baffle 22 and the lower baffle 12 constitute the anti-release mechanism. The upper baffle 22 abuts against the lower baffle 12, so that the rib 10 is limited in the groove 20 to define a maximum degree to which the upper half box body 1 and the lower half box body 2 can be unfolded.

The positioning mechanism in the present invention, as shown in the figures, is not limited to the structure shown in the figures. Specifically, the positioning mechanism includes the rack track 23, the toothed block 3 and the pressing block 4. The rib 11 of the upper half box body 1 has a hollow tube.

The bottom of the hollow tube is closed and the top of the hollow tube has the opening 13. The opening 13 is located on the top surface of the upper half box body 1. The side surface at the bottom of the hollow tube has the side opening 14. The rack track 23 is formed on the inner wall of the groove 21 of the lower half box body 2 corresponding to the side opening 14 at the bottom of the hollow tube. The toothed block 3 is disposed at the bottom of the hollow tube. The elastic member 33 (such as a spring) is disposed between the toothed block 3 and the inner wall of the hollow tube. Under the action of the elastic member 33, the engaging tooth 31 of the toothed block 3 extends out from the side opening 14 at the bottom of the hollow tube, and the engaging tooth 31 fits with the rack track 23. The lower inclined pushing surface 32 is formed on the upper portion of the toothed block 3. The pressing block 4 is inserted into the hollow tube. The upper end of the pressing block 4 is located at the opening 13 of the hollow tube to facilitate a pressing operation. The upper inclined pushing surface 41 is formed at the lower end of the pressing block 4. The upper inclined pushing surface 41 fits with the lower inclined pushing surface 32, so that when the pressing block 4 is pressed, the toothed block 3 is driven to overcome the action of the elastic member 33, so that the engaging tooth 31 is separated from the rack track 23. At this time, the upper half box body 1 is liftable relative to the lower half box body 2.

In the present invention, the positioning mechanism is further optimally designed in the following manner. The guide block 34 is formed in the middle of the upper portion of the toothed block 3, and the lower inclined pushing surface 32 is formed on each of both sides of the guide block 34. The guide groove 42 is formed in the middle of the lower end of the pressing block 4, and the upper inclined pushing surface 41 is formed on each of both sides of the guide groove 42. When the upper inclined pushing surface 41 fits with the lower inclined pushing surface 32, the guide block 34 is located in the guide groove 42 to guide the toothed block 3 and the pressing block 4 to ensure the accuracy of the pressing action. Further, the mounting opening 15, the cover plate 151 and the mounting block 16 are formed at a lower section of the hollow tube. The cover plate 151 is disposed at the mounting opening 15. The side opening 14 from which the engaging tooth 31 extends out is located under the cover plate 151. The cover plate 151 is fixed on the mounting block 16 by the fastener 152 such as a screw. The mounting block 16 is located above the toothed block 3 and in the guide groove 42 of the pressing block 4 to further guide the pressing block 4, thereby ensuring the accuracy of the pressing action. Further, the limiting step 17 is formed at the inner wall of the hollow tube. The limiting convex ring 43 is formed at the outer surface of the pressing block 4. The limiting step 17 fits with the limiting convex ring 43, so that the pressing block 4 is limited in the hollow tube to prevent the pressing block 4 from being separated.

The disinfection box of the present invention is further designed in the following manner. The upper arc edge 18 is formed on the upper half box body 1, and the lower arc edge 24 is formed on the lower half box body 2. When the upper half box body 1 and the lower half box body 2 are folded, the upper arc edge 18 is attached to the lower arc edge 24, and the forcing grooves 181 and 241 are formed at positions of the upper arc edge 18 and the lower arc edge 24 corresponding to the pressing block 4. When performing a pressing operation, a thumb presses the pressing block 4, while the remaining fingers extend into the forcing grooves 181 and 241 to easily lift up or press down the upper half box body 1, which is convenient to use.

Specifically, the disinfection box of the present invention is provided with an opening on the top surface of the upper half box body 1. The chamber door 19 covers the opening, and the opening is configured to facilitate placing or removing the objects. The position of the chamber door 19 is not limited to the figures. For example, when the disinfection box has an adequate height after being unfolded, the chamber door 19 can also be disposed at a side surface.

The disinfection box of the present invention adopts ozone disinfection, ultraviolet disinfection or other disinfection methods. For example, a battery, the switch 25, a circuit board and an ultraviolet generator are mounted at the bottom of the lower half box body 2. The battery, the circuit board and the ultraviolet generator are conventional devices, and thus are not shown in the figures. The battery adopts an ordinary battery or a rechargeable battery. The battery supplies power to the circuit board and the ultraviolet generator through the switch 25. The circuit board controls the ultraviolet generator to work or stop.

The above is only the preferred embodiment of the present invention, but the design concept of the present invention is not limited thereto. Any non-substantive modifications of the present invention using this concept, that is, various changes made to the present invention in forms and details, shall fall within the scope of protection of the present invention.

What is claimed is:

1. A liftable and foldable disinfection box, comprising
an upper half box body and a lower half box body; wherein
the upper half box body is sleeved on the lower half box body in a relatively liftable manner;
a positioning mechanism is mounted on the upper half box body;
the upper half box body and the lower half box body are fixed by locking the positioning mechanism, or the upper half box body is liftable relative to the lower half box body by unlocking the positioning mechanism;
a disinfection chamber is formed between the upper half box body and the lower half box body,
the disinfection chamber has a chamber door;
the relatively liftable manner comprises:
sleeving a peripheral side wall of the upper half box body outside a peripheral side wall of the lower half box body,
forming a rib and a groove fitting with each other on the peripheral side wall of the upper half box body and the peripheral side wall of the lower half box body, wherein the rib and the groove extend along a vertical direction, and the rib is slidably fitted in the groove to enable the upper half box body to be liftable relative to the lower half box body;
a plurality of sets of ribs and grooves are formed on the upper half box body and the lower half box body, and the plurality of sets of ribs and grooves are evenly distributed on the peripheral side wall of the upper half box body and the peripheral side wall of the lower half box body;
the positioning mechanism is mounted on at least one set of the plurality of sets of ribs and grooves,
an anti-release mechanism is mounted on the at least one set of the plurality of sets of ribs and grooves,
an upper portion of the groove is provided with an upper baffle, and a lower portion of the rib is provided with a lower baffle,
the upper baffle and the lower baffle constitute the anti-release mechanism; and the upper baffle abuts against the lower baffle, and the rib is limited in the groove.

2. A liftable and foldable disinfection box, comprising an upper half box body and a lower half box body; wherein the upper half box body is sleeved on the lower half box body in a relatively liftable manner;

a positioning mechanism is mounted on the upper half box body;

the upper half box body and the lower half box body are fixed by locking the positioning mechanism, or the upper half box body is liftable relative to the lower half box body by unlocking the positioning mechanism;

a disinfection chamber is formed between the upper half box body and the lower half box body, the disinfection chamber has a chamber door, the positioning mechanism comprises a rack track, a toothed block and a pressing block;

a rib is formed on the upper half box body, and the rib has a hollow tube;

a bottom of the hollow tube is closed and a top of the hollow tube has an opening;

the opening is located on a top surface of the upper half box body;

a side surface at the bottom of the hollow tube has a side opening;

the lower half box body has a groove, and the rack track is formed on an inner wall of the groove, wherein the inner wall of the groove corresponds to the side opening at the bottom of the hollow tube;

the toothed block is disposed at the bottom of the hollow tube;

an elastic member is disposed between the toothed block and an inner wall of the hollow tube;

under an action of the elastic member, an engaging tooth of the toothed block extends out from the side opening at the bottom of the hollow tube and the engaging tooth fits with the rack track;

a lower inclined pushing surface is formed on an upper portion of the toothed block;

the pressing block is inserted into the hollow tube;

an upper end of the pressing block is located at the opening of the hollow tube;

an upper inclined pushing surface is formed at a lower end of the pressing block;

the upper inclined pushing surface fits with the lower inclined pushing surface, when the pressing block is pressed, the toothed block is driven to overcome the action of the elastic member, and the engaging tooth is separated from the rack track.

3. The liftable and foldable disinfection box of claim 2, wherein a guide block is formed in a middle of the upper portion of the toothed block, and the lower inclined pushing surface is formed on each of both sides of the guide block;

a guide groove is formed in a middle of the lower end of the pressing block, and the upper inclined pushing surface is formed on each of both sides of the guide groove; and when the upper inclined pushing surface fits with the lower inclined pushing surface, the guide block is located in the guide groove.

4. The liftable and foldable disinfection box of claim 3, wherein a mounting opening, a cover plate and a mounting block are formed at a lower section of the hollow tube;

the cover plate is disposed at the mounting opening;

the side opening is located under the cover plate, and the engaging tooth extends out from the side opening;

the cover plate is fixed on the mounting block by a fastener, and the mounting block is located above the toothed block and in the guide groove of the pressing block.

5. The liftable and foldable disinfection box of claim 2, wherein a limiting step is formed at the inner wall of the hollow tube, and a limiting convex ring is formed at an outer surface of the pressing block; and the limiting step fits with the limiting convex ring, and the pressing block is limited in the hollow tube.

6. The liftable and foldable disinfection box of claim 2, wherein an upper arc edge is formed on the upper half box body, and a lower arc edge is formed on the lower half box body;

when the upper half box body and the lower half box body are folded, the upper arc edge is attached to the lower arc edge, and a forcing groove is formed at each of a position of the upper arc edge and a position of the lower arc edge, wherein the position of the upper arc edge and the position of the lower arc edge correspond to the pressing block, and a hand extends into the forcing groove.

7. The liftable and foldable disinfection box of claim 1, wherein a battery, a switch, a circuit board and an ultraviolet generator are mounted at a bottom of the lower half box body, the battery supplies power to the circuit board and the ultraviolet generator through the switch, and the circuit board controls the ultraviolet generator to work or stop.

* * * * *